United States Patent
Sawant et al.

(10) Patent No.: US 9,133,094 B2
(45) Date of Patent: Sep. 15, 2015

(54) APPARATUS AND PROCESS FOR NITRATION SELECTIVITY FLEXIBILITY ENABLED BY AZEOTROPIC DISTILLATION

(75) Inventors: Mahesh Sawant, Pune (IN); Daniel M. Trauth, Crystal Lake, IL (US); John G. Pendergast, Jr., Lake Jackson, TX (US)

(73) Assignee: ANGUS CHEMICAL COMPANY, Buffalo Grove, IL (US)

( * ) Notice: Subject to any disclaimer, the term of this patent is extended or adjusted under 35 U.S.C. 154(b) by 0 days.

(21) Appl. No.: 14/007,531

(22) PCT Filed: Apr. 5, 2012

(86) PCT No.: PCT/US2012/032277
§ 371 (c)(1),
(2), (4) Date: Sep. 25, 2013

(87) PCT Pub. No.: WO2012/148643
PCT Pub. Date: Nov. 1, 2012

(65) Prior Publication Data
US 2014/0031594 A1    Jan. 30, 2014

(30) Foreign Application Priority Data

Apr. 18, 2011  (IN) ............................ 1329/CHE/2011

(51) Int. Cl.
*C07C 205/02* (2006.01)
*C07C 201/08* (2006.01)
*C07C 201/16* (2006.01)

(52) U.S. Cl.
CPC ............. *C07C 205/02* (2013.01); *C07C 201/08* (2013.01); *C07C 201/16* (2013.01)

(58) Field of Classification Search
CPC .... C07C 205/02; C07C 201/16; C07C 201/08
USPC .......................................... 568/947; 422/187
See application file for complete search history.

(56) References Cited

U.S. PATENT DOCUMENTS

| | | | |
|---|---|---|---|
| 1,917,391 | A | 7/1933 | Othmer |
| 2,050,234 | A | 8/1936 | Othmer |
| 2,489,320 | A | 11/1949 | Nygaard et al. |
| 4,476,336 | A | 10/1984 | Sherwin |
| 4,626,607 | A | 12/1986 | Jacquinot et al. |
| 4,661,208 | A | 4/1987 | Honma |
| 4,766,257 | A | 8/1988 | Wang |
| 2011/0092750 | A1* | 4/2011 | Trauth et al. .................. 568/948 |

FOREIGN PATENT DOCUMENTS

| | | |
|---|---|---|
| FR | 918462 A | 2/1947 |
| GB | 298137 A | 9/1929 |

(Continued)

OTHER PUBLICATIONS

International Application No. PCT/US2012/032277, International Preliminary Report on Patentability, Oct. 22, 2013.

(Continued)

*Primary Examiner* — Jafar Parsa
*Assistant Examiner* — Amy C Bonaparte
(74) *Attorney, Agent, or Firm* — Foley & Lardner LLP

(57) ABSTRACT

Disclosed are processes and apparatuses for concentrating at least one organic acid using an alkyl acetate as an entrainer. The processes and apparatuses may use the same alkyl acetate as an entrainer to concentrate a mixture of organic acids.

10 Claims, 4 Drawing Sheets

(56) References Cited

FOREIGN PATENT DOCUMENTS

| JP | 61-109750 | | 5/1986 |
|----|-----------|---|--------|
| WO | 2009013623 | A2 | 1/2009 |
| WO | WO2009129097 | * | 10/2009 |
| WO | 2012078725 | A1 | 6/2012 |

OTHER PUBLICATIONS

International Application No. PCT/US2012/032277, Notification of Transmittal of the International Search Report and the Written Opinion of the International Searching Authority, Sep. 17, 2012.

Notice of Reasons for Rejection on Japanese Application 2014-506439, mailed Nov. 4, 2014.

* cited by examiner

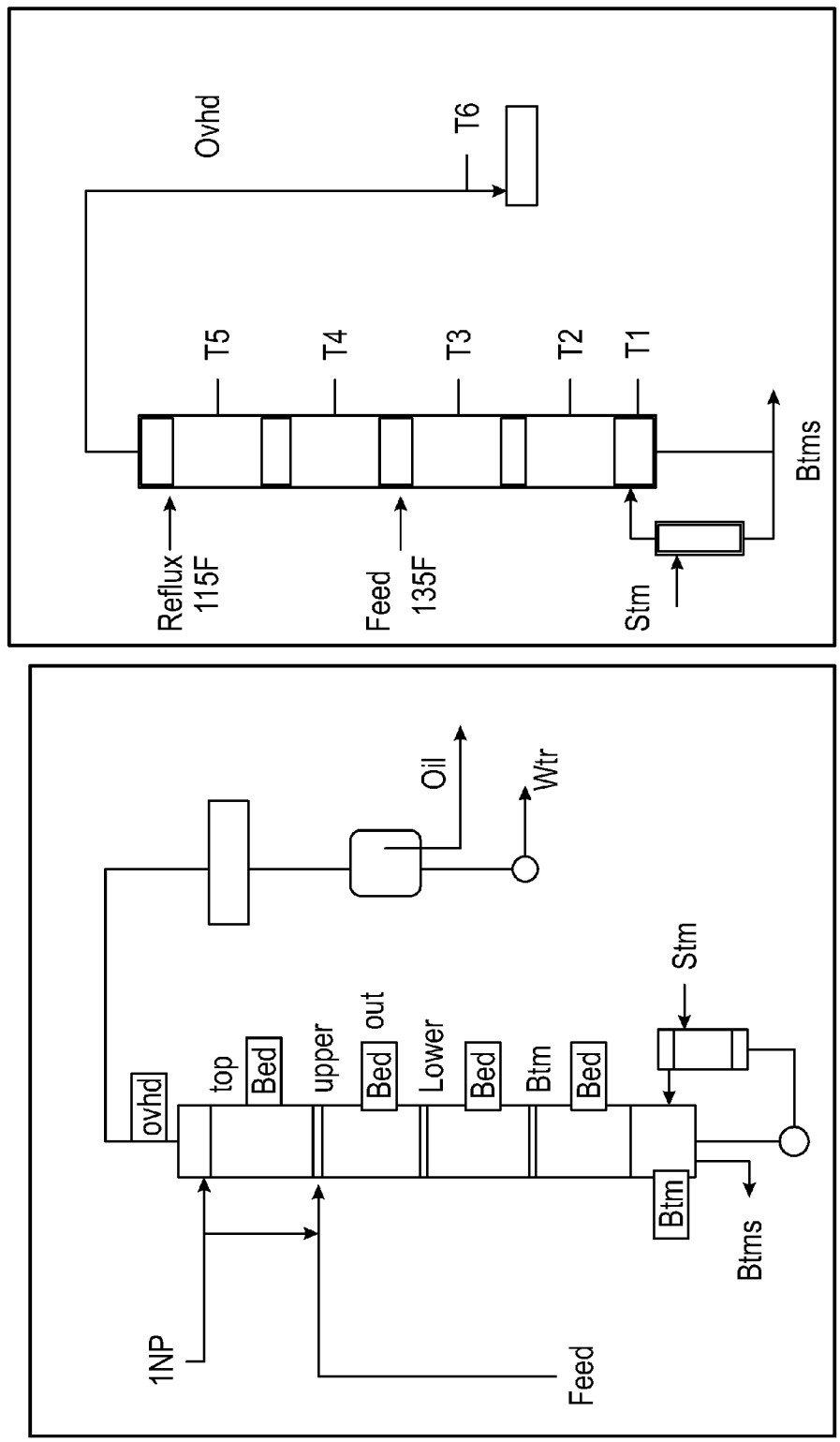

9,133,094 B2

APPARATUS AND PROCESS FOR NITRATION SELECTIVITY FLEXIBILITY ENABLED BY AZEOTROPIC DISTILLATION

CROSS REFERENCE TO RELATED APPLICATION

This application claims priority to International Patent Application No. PCT/US2012/032277, filed Apr. 5, 2012, which claims priority to Indian Provisional Application No. 1329/CHE/2011, filed Apr. 18, 2011, all of which are hereby incorporated herein by reference in their entireties.

FIELD

This invention relates to azeotropic distillation in high pressure nitration processes. More specifically, this invention relates to processes and apparatuses for the azeotropic removal of water from an organic acid stream produced during nitroalkane synthesis when the organic acid stream comprises more than one organic acid.

BACKGROUND

In a high pressure nitration process, a hydrocarbon, such as propane, and an organic acid, such as acetic acid, propionic acid, and/or butyric acid, reacts with aqueous nitric acid to yield products such as nitromethane, 1-nitropropane, and 2-nitropropane. In addition, the process produces a significant amount of water and some organic acids. Many of the organic acids fed to the reactor are not converted in a single pass through the reactor. Thus, in order to recycle the organic acids back to the reactor, much of the water needs to be removed. Because the relative volatility between acetic acid and water is low, conventional distillation is energy-consuming and costly. In addition, propionic and n-butyric acid form low-boiling azeotropes with water, resulting in unavoidable acid losses in the distillation overhead if conventional distillation is used. In addition, more than one organic acid may need to be recycled back to the reactor. A need exists, therefore, for economical and energy-efficient processes for the removal of water from organic acid streams comprising multiple organic acids.

BRIEF SUMMARY

In one aspect, an illustrative embodiment provides a process comprising reacting a hydrocarbon feedstock with an aqueous feedstock in a reactor to produce a product stream comprising a nitroalkane and byproducts; processing the product stream to produce a first top stream and a first bottom stream, wherein the first top stream comprises the nitroalkane and the first bottom stream comprises at least a first organic acid and water. The process further comprises supplying the first bottom stream to an azeotropic distillation column; using an alkyl acetate as an entrainer in the azeotropic distillation column, such that the first bottom stream is separated into at least a second top stream and a second bottom stream, wherein the second top stream comprises the alkyl acetate and water and wherein the second bottom stream comprises the first organic acid; separating the second top stream in a phase separator into an organic phase and an aqueous phase, the organic phase comprising the alkyl acetate; and returning at least a portion of the organic phase to the azeotropic distillation column.

In another aspect, an illustrative embodiment provides a process comprising reacting a hydrocarbon feedstock with an aqueous feedstock in a reactor in a high pressure nitration process to produce a product stream comprising a nitroalkane and byproducts, wherein the aqueous feedstock comprises water, nitric acid, at least a first organic acid, and at least a second organic acid; processing the product stream to produce a first top stream and a first bottom stream, wherein the first top stream comprises the nitroalkane and the first bottom stream comprises the first organic acid, the second organic acid, and water. The process further comprises supplying the first bottom stream to an azeotropic distillation column; using an alkyl acetate as an entrainer in the azeotropic distillation column, such that the first bottom stream is separated into at least a second top stream and a second bottom stream, wherein the second top stream comprises the alkyl acetate and water and wherein the second bottom stream comprises the first organic acid and the second organic acid; separating the second top stream in a phase separator into an organic phase and an aqueous phase, the organic phase comprising the alkyl acetate; and returning at least a portion of the organic phase to the azeotropic distillation column.

In another aspect, an illustrative embodiment provides an apparatus comprising a reactor for reacting a hydrocarbon feedstock and an aqueous feedstock in a high pressure nitration process to produce a product stream comprising a nitroalkane and byproducts, wherein the aqueous feedstock comprises water, nitric acid, at least a first organic acid, and at least a second organic acid; at least one degasser for degassing the product stream to produce a liquid stream; and at least one stripping apparatus for separating the liquid stream into a first top stream and first bottom stream, wherein the first top stream comprises the nitroalkane and the first bottom stream comprises the first organic acid, the second organic acid, and water. The apparatus further comprises an azeotropic distillation column configured to use an alkyl acetate as an entrainer to separate the first bottom stream into a second top stream and a second bottom stream, wherein the second top stream comprises the alkyl acetate and water, and wherein the second bottom stream comprises the first organic acid and the second organic acid; and a phase separator configured to separate the second top stream into an organic phase and an aqueous phase, the organic phase comprising the alkyl acetate.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 3 is a schematic diagram of a distillation column used for Example 7.

FIG. 4 is a schematic diagram of a distillation column used for Example 7, showing the location of temperature probes.

DETAILED DESCRIPTION

Figure 1:
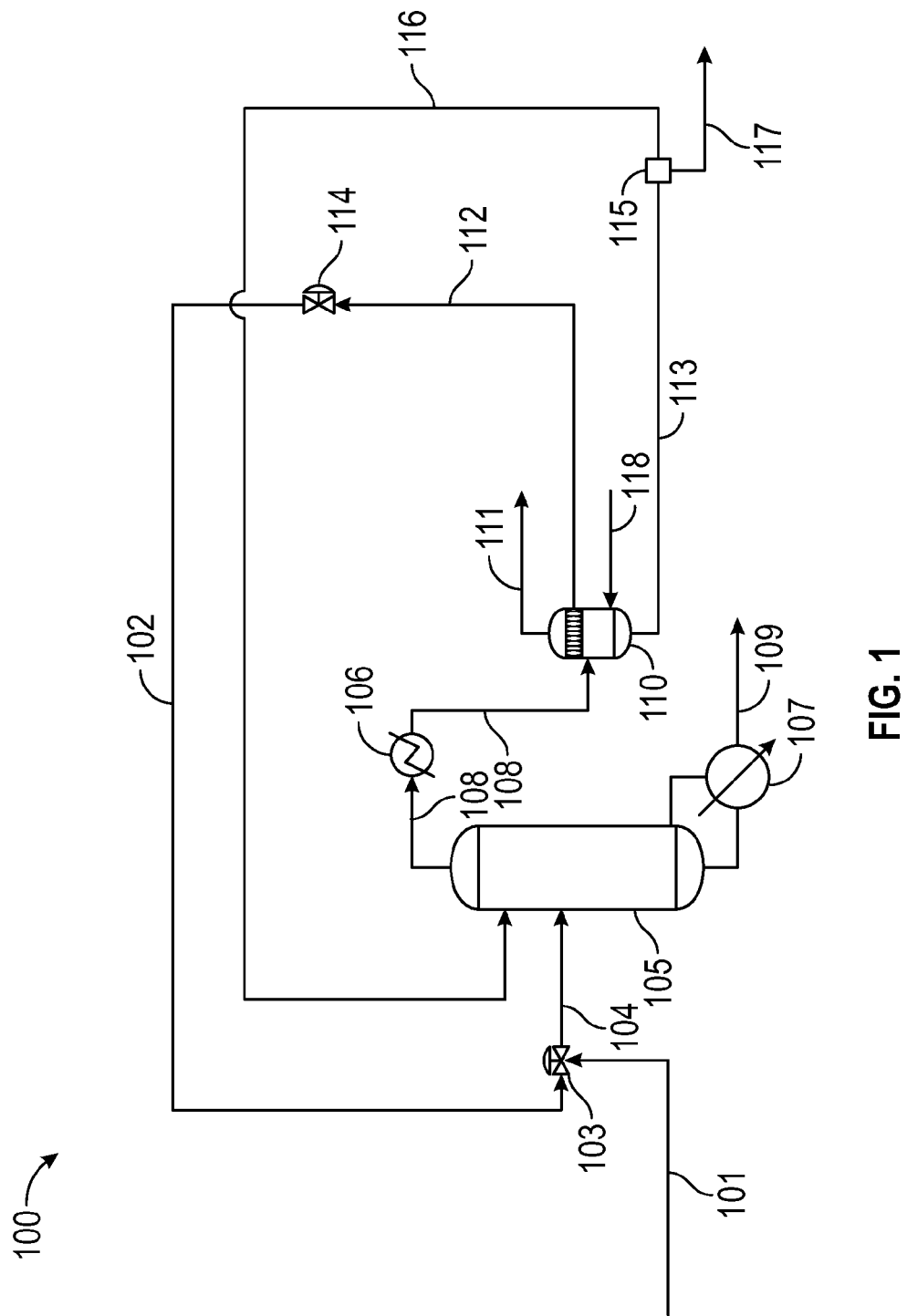
FIG. 1 is a schematic diagram of an apparatus for removing water from an organic acid solution, in accordance with an illustrative embodiment.

In one aspect, a process is provided for using an alkyl acetate as an entrainer in an azeotropic distillation column in order to remove water from an aqueous organic acid solution. FIG. 1 illustrates an apparatus 100 for removing water from an aqueous organic acid solution. A first aqueous phase 101 may be combined with an organic phase 102 at a first control valve 103 to form a feed stream 104. The first aqueous phase 101 may comprise water and at least one organic acid. The organic acid may be acetic acid, propionic acid, butyric acid, hexanoic acid, another carboxylic acid, or any combination thereof. In preferred embodiments, the first aqueous phase 101 comprises at least two different organic acids. For example, the first aqueous phase 101 may comprise acetic acid and propionic acid or propionic acid and butyric acid. In other preferred embodiments, the first aqueous phase 101 comprises at least three different organic acids. For example, the first aqueous phase 101 may comprise acetic acid, propionic acid and butyric acid. The organic phase 102 may comprise at least one alkyl acetate. The alkyl acetate may be, for example, isopropyl acetate, n-butyl acetate, or isobutyl acetate.

The feed stream 104 may be supplied to an azeotropic distillation column 105. In alternative embodiments, the first aqueous phase 101 and the organic phase 102 may be supplied directly to the azeotropic distillation column 105. The azeotropic distillation column 105 may be, for example, a heterogenous azeotropic distillation (HAD) column (acid drying column (ADC)). The azeotropic distillation column 105 may comprise a condenser 106 and a reboiler 107.

In the azeotropic distillation column 105, the alkyl acetate may be used as an entrainer, such that the feed stream 104 is separated into at least a top stream 108 and a bottom stream 109. The top stream 108 may comprise the alkyl acetate and water. The bottom stream 109 may comprise the at least one organic acid. The concentration of the organic acid(s) in the bottom stream 109 may be about 70 weight percent or greater, more preferably about 80 weight percent or greater, and most preferably about 85 weight percent or greater. Further, the concentration of the organic acid(s) in the bottom stream 109 may be about 98 weight percent or less, more preferably about 95 weight percent or less, and most preferably about 90 weight percent or less.

The top stream 108 may enter a phase separator 110. The phase separator 110 may be a decanter. The phase separator 110 may separate the top stream 108 into a gas phase 111, an organic phase 112, and a second aqueous phase 113. At least a portion of the organic phase 112 may pass through a second control valve 114 as the organic phase 102, which may be returned to the distillation column 104 or to the first control valve 103. The second aqueous phase 113 may be divided in a divider 115 into a recycled aqueous phase 116 and a discharged aqueous phase 117. The recycled aqueous phase 116 may be returned to the distillation column 105. The percentage of the second aqueous phase 113 that is returned to the distillation column 105 as the recycled aqueous phase 116 may be about 40 percent or greater, more preferably about 44 percent or greater, and most preferably about 45 percent or greater. Further, the percentage of the second aqueous phase 113 that is returned to the distillation column 105 as the recycled aqueous phase 116 may be about 60 percent or less, more preferably about 54 percent or less, and most preferably about 47 percent or less.

Additional entrainer may be added to the phase separator 110 through an entrainer make-up stream 118. The amount of additional entrainer may be added to balance the amount of entrainer removed or lost in the bottom stream 109 and/or the discharged aqueous phase 117.

Figure 2:
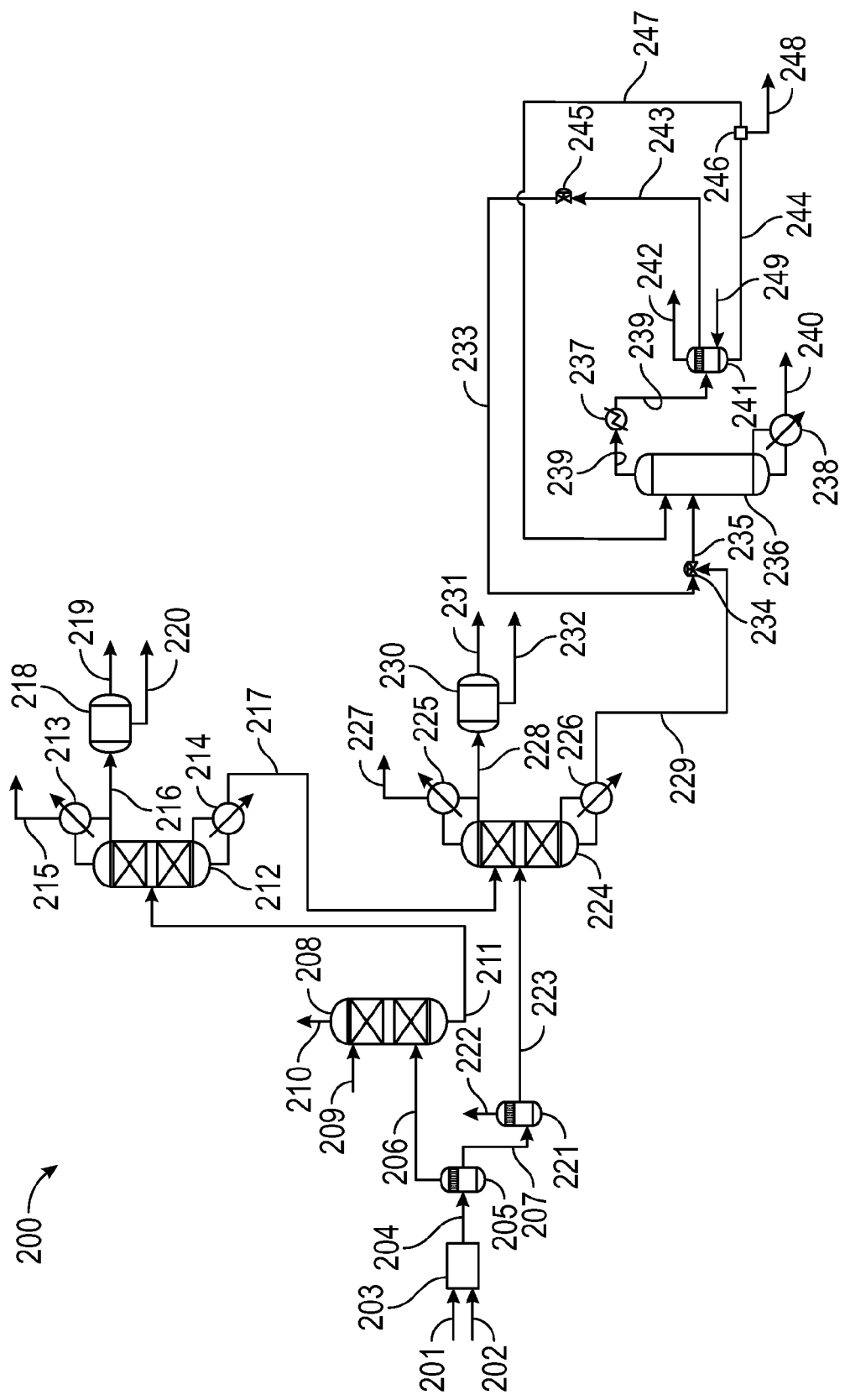
FIG. 2 is a schematic diagram of an apparatus for producing a nitroalkane and for removing water from an organic acid solution, in accordance with an illustrative embodiment.

FIG. 2 illustrates an apparatus 200 for removing water from an aqueous organic acid solution, wherein the organic acid solution is a byproduct of a high pressure nitration process. The high pressure nitration process uses a mixed phase reactor system—including both a liquid phase and a vapor phase. The use of the higher operating pressure results in a distinct liquid phase in the reactor. A hydrocarbon feedstock 201 and aqueous feedstock 202 may be introduced into a reactor 203. The hydrocarbon feedstock 201 may include, without limitation, propane, cyclohexane, isobutane, or n-octane. The aqueous feedstock 202 may include, without limitation, water, nitric acid, and at least one organic acid, such as acetic acid, propionic acid, butyric acid, hexanoic acid, another carboxylic acid, or any combination thereof. In preferred embodiments, the aqueous feedstock 201 comprises at least two different organic acids. For example, the aqueous feedstock 201 may comprise acetic acid and propionic acid or propionic acid and butyric acid. In other preferred embodiments, the aqueous feedstock 201 comprises at least three different organic acids. For example, the aqueous feedstock 201 may comprise acetic acid, propionic acid and butyric acid.

The hydrocarbon feedstock 201 and the aqueous feedstock 202 may react in a reactor 203 at a reactor pressure and a reaction temperature, such that a reaction product stream 204 comprising nitrated compounds and byproducts may be formed. The reaction product stream 204 may comprise at least one product nitroalkane. For example, when the hydrocarbon feedstock 201 comprises propane, the reaction product stream 204 may include one or more nitropropanes, including but not limited to 1-nitropropane, 2-nitropropane, and/or 2,2-dinitropropane. When the hydrocarbon feedstock 201 comprises cyclohexane, the reaction product stream 204 may include nitrocyclohexane. When the hydrocarbon feedstock 201 comprises isobutane, the reaction product stream 204 may include tert-nitrobutane. When the hydrocarbon feedstock 201 comprises n-octane, the reaction product stream may include nitro-n-octane.

The hydrocarbon feedstock 201 and the aqueous nitric acid 202 may be mixed, or partially mixed, prior to entry into the reactor 203, or alternatively; they may be added individually, with mixing to occur within the reactor 203. In addition, the hydrocarbon feedstock 201 and the aqueous nitric acid 202, whether added together or individually, may be preheated prior to entry into the reactor 203.

The aqueous nitric acid in the aqueous feedstock 202 may be delivered to the reactor 203 in the form of an aqueous solution that contains at least about 10 weight percent, more preferably at least about 15 weight percent, most preferably at least about 20 weight percent, of the acid. Further, the solution may contain less than about 50 weight percent, more preferably less than about 40 weight percent, and most preferably less than about 35 weight percent, of the acid. In other embodiments, the nitric acid solution may contain between about 15 and about 40 weight percent of the acid. In further embodiments, the nitric acid solution may contain between about 18 and about 35 weight of the acid.

The organic acid(s) in the aqueous feedstock 202 may be delivered to the reactor 203 in the form of an aqueous solution that contains at least about 15 weight percent, more preferably at least about 40 weight percent, of the organic acid(s).

The mole ratio of the hydrocarbon feedstock 201 to the aqueous nitric acid 202 may be at least about 0.3:1, more preferably at least about 0.5:1.

In the high pressure nitration process, the reactor pressure may be at least about $3.4 \times 10^6$ Pascal (500 psi), more preferably at least about $6.8 \times 10^6$ Pascal (1000 psi), and most preferably at least about $8.3 \times 10^6$ Pascal (1200 psi). In some embodiments, the pressure may be about $11.0 \times 10^6$ Pascal (1600 psi) or less, more preferably about $10.3 \times 10^6$ Pascal (1500 psi) or less, most preferably about $9.7 \times 10^6$ Pascal (1400 psi) or less. In other embodiments, the pressure may be between about $6.8 \times 10^6$ Pascal (1000 psi) and $9.7 \times 10^6$ Pascal (1400 psi). Various methods known in the art may be used for maintaining the pressure within the desired range including, for example, through the use of a back-pressure regulator.

The reaction temperature within the reactor 203 may be controlled (for example with heat exchange fluid or using heat generated from the reaction) to at least about 140 degrees Celsius and to less than about 325 degrees Celsius. In other embodiments, the temperature may be at least about 215 degrees Celsius and to less than about 325 degrees Celsius. In some embodiments, the temperature may be at least about 180 degrees, at least about 200 degrees, at least about 230 degrees, or at least about 240 degrees. In other embodiments, the temperature may be less than about 290 degrees, less than about 280 degrees, less than about 270 degrees, or less than about 250 degrees. In further embodiments, the temperature may be between about 200 and 250 degrees Celsius. In yet further embodiments, the temperature may be between about 215 and 280 degrees Celsius, or between about 220 and 270 degrees Celsius.

The residence time of the reactants in the reactor 203 may be preferably at least about 30 seconds, more preferably at least about 90 seconds. Residence time may be controlled in various ways including, for example, by the length and/or width of the reactor or through the use of packing material. Residence time may be determined by dividing the volume of the reactor by the inlet flow rates.

The reactor 203 may be a downflow configured reactor. That is, the reactor, which is preferably of an elongated and linear shape, such as a tube shape, may be positioned so that reactants are added through an entry port at or near the top of the reactor and then flow down the reactor for a residence time that is sufficient to allow reaction to occur and formation of the desired product. The product mixture may be collected through an exit port at or near the bottom of the reactor.

The operation of the reactor in a downflow configuration provides certain advantages over prior art systems, which generally utilize a horizontal, upflow, coiled or a batch autoclave type apparatus. In particular, the downflow configuration of the invention provides nitrated compounds that contain relatively low levels of oxidation byproducts as compared to such prior art systems.

Without wishing to be bound by any particular theory, it is believed that the advantages of the downflow reactor result primarily from its ability to minimize the amount and residence time of the liquid phase within the reactor. The liquid phase in general contains a low mole ratio of hydrocarbons to nitric acid. This low mole ratio favors oxidation chemistry at the expense of nitration and oxidation therefore primarily occurs in the liquid phase. In a downflow reactor (also referred to as a trickle bed reactor) the gas is the continuous phase and the liquid trickles down the reactor walls or packing Therefore, the amount of liquid phase(s) in a downflow configured reactor is maintained at a low level and consequently oxidation chemistry is minimized.

In contrast, in an upflow reactor, also referred to as a bubble column, the liquid is the continuous phase (and bubbles rise quickly through the continuous liquid phase). Thus, an upflow reactor maximizes the liquid holdup. Because, as noted above, oxidation primarily occurs in the liquid phase, the upflow reactor maximizes the formation of oxidation byproducts. Similarly, coil and horizontal reactor configurations also increase liquid residence time and therefore oxidation chemistry as compared to a downflow reactor. A further disadvantage of coiled reactors is that they are not well-suited for industrial scale production because of the difficulty of fabricating large scale reactors in this shape.

The reactor 203 may also be packed with a packing material to improve reactant mixing and heat transfer and/or to vary the reactor volume. Packing of the reactor may be preferred, for example, in a propane nitration system where it is desired to increase the concentration of 2,2-dinitropropane in the reaction product stream. Suitable packing materials may include, for example, glass beads, random packing, or structured packing, such as those typically employed in distillation devices. Other packing materials are known in the art and may be used. The reactor 203 may also be an un-packed reactor.

The reaction product stream 204 then may enter a first degasser 205. The first degasser 205 may separate the reaction product stream 204 into a first gas phase 206 and a first liquid phase 207. The first gas phase 206 may be sent to an absorber 208. The absorber 208 may use a recycled water stream 209 to absorb any nitroalkanes in the first gas phase 206, such that a second gas phase 210 and a second liquid phase 211 are formed. In an illustrative embodiment, the recycled water in the recycled water stream 209 may be recycled from a downstream nitroalkane recovery process.

The second liquid phase 211 may be sent to a first stripping apparatus 212 in order to recover the least one product nitroalkane. The first stripping apparatus 212 may comprise a first condenser 213 and a first reboiler 214. The first stripping apparatus 212 may strip oil-soluble components from the second liquid phase 211, such that a second gas phase 215, a first oil phase 216, and a first aqueous phase 217 are formed. The first oil phase 216 may be sent to a first separator 218. The first separator 218 may be, for example, a conventional distillation column. The first separator 218 may separate the first oil phase 218 into at least a second oil phase 219 and a second aqueous phase 220. The second oil phase 219 may comprise the at least one product nitroalkane.

The first liquid phase 207 from the first degasser 205 may then enter a second degasser 221. The second degasser 221 may phase separate the first liquid phase 207 into a third gas phase 222 and a third liquid phase 223. In some illustrative embodiments, the high concentration of acetic acid may co-solubilize the nitroalkane products such that a single liquid phase 223, results rather than an oil phase and an aqueous phase. The liquid phase 223 may comprise the at least one product nitroalkane and at least one organic acid.

The liquid phase 223 may then be sent to a second stripping apparatus 224. The second stripping apparatus 224 may comprise a second condenser 225 and a second reboiler 226. The second stripping apparatus 224 may strip oil-soluble components from the third liquid phase 223, such that a fourth gas phase 227, a third oil phase 228, and a third aqueous phase 229 are formed. The third oil phase 228 may be sent to a second separator 230. The second separator 230 may be, for example, a conventional distillation column. The second separator 230 may separate the third oil phase 228 into at least a fourth oil phase 231 and a fourth aqueous phase 232. The third oil phase 231 may comprise the at least one product nitroalkane.

The third aqueous phase 229 may comprise water and at least one organic acid. The organic acid may be acetic acid, propionic acid, butyric acid, another carboxylic acid, or any combination thereof. In preferred embodiments, the third aqueous phase 229 comprises at least two organic acids. In other preferred embodiments, the third aqueous phase 229 comprises at least three different organic acids. The third aqueous phase 229 may be combined with an organic phase 233 at a first control valve 234 to form a feed stream 235. The organic stream 233 may comprise at least one alkyl acetate. The alkyl acetate may be, for example, isopropyl acetate, n-butyl acetate, or isobutyl acetate.

The feed stream 235 may be sent to a distillation column 236, such as a heterogeneous azeotropic distillation column. Heterogeneous azeotropic distillation columns may be used to separate mixtures of close relative volatility and also to break up azeotropes. The distillation column 236 may comprise a third condenser 237 and a third reboiler 238. In the distillation column 236, the alkyl acetate may be used as an entrainer, such that the feed stream 235 is separated into at least a top stream 239 and a bottom stream 240. The top stream 239 may comprise the alkyl acetate and water. The bottom stream 240 may comprise the organic acid(s). The concentration of the organic acid(s) in the bottom stream 240 may be about 70 weight percent or greater, more preferably about 80 weight percent or greater, and most preferably about 85 weight percent or greater. Further, the concentration of the organic acid(s) in the bottom stream 240 may be about 98 weight percent or less, more preferably about 95 weight percent or less, and most preferably about 90 weight percent or less. The bottom stream 240 may be returned to the reactor 203 as an organic acid diluent in the hydrocarbon feedstock 201. In alternative embodiments, the bottom stream 240 may be used for other purposes, such as in other processes.

The top stream 239 may enter a phase separator 241. The phase separator 241 may be a decanter. The phase separator 241 may separate the top stream 229 into a fifth gas phase 242, an organic phase 243, and a fourth aqueous phase 244. At least a portion of the organic phase 244 may pass through a second control valve 245 as the organic phase 233, which may be returned to the distillation column 236 or to the first control valve 234. The fourth aqueous phase 244 may be divided in a divider 246 into a recycled aqueous phase 247 and a discharged aqueous phase 248. The recycled aqueous phase 247 may be returned to the distillation column 236. The percentage of the fourth aqueous phase 244 that is returned to the distillation column 236 as the recycled aqueous phase 247 may be about 40 percent or greater, more preferably about 44 percent or greater, and most preferably about 45 percent or greater. Further, the percentage of the fourth aqueous phase 244 that is returned to the distillation column 236 as the recycled aqueous phase 247 may be about 60 percent or less, more preferably about 54 percent or less, and most preferably about 47 percent or less.

Additional entrainer may be added to the phase separator 241 through an entrainer make-up stream 249. The amount of additional entrainer may be added to balance the amount of entrainer removed or lost in the bottom stream 240 and/or the discharged aqueous phase 248.

EXAMPLES

Various examples are demonstrated. Examples 1-6 are generated using ASPEN computer-aided process simulation software (Aspen Technology, Incorporated, Burlington, Mass.), which uses a database of measured physical properties for engineering design calculations. Example 7 is from an experiment at a development plant.

Simulation

Examples 1-6 are generated using ASPEN computer-aided process simulation software. Propane, nitric acid, and organic acid(s) react in a reactor to produce a product stream comprising nitroalkanes (nitromethane, 1-nitropropane, 2-nitropropane, 2,2-dinitropropane, nitroethane) and oxidation byproducts (acetic acid, propionic acid, butyric acid). The product stream also contains off-gases, such as nitrous oxide, nitric oxide, carbon dioxide, carbon monoxide, unconverted propane and water.

The product stream is degassed in two successive degassers. The gas stream from the first degasser is then separated in an absorber (scrubbed with recycled water, for example, water from a step in the downstream nitroalkane recovery process) such that a gaseous phase and an aqueous phase are formed. The aqueous phase from the absorber is sent to a first stripping apparatus, where a small amount of recovered nitroparaffins are removed. The aqueous phase from the second degasser and the aqueous phase from the first stripping apparatus are sent to a second stripping apparatus. There, the nitroalkanes are stripped from the aqueous phases, so that the bottoms from the stripping apparatus comprise water and dissolved organic acids. The bottoms from the second stripping apparatus typically comprise around 60 weight percent organic acid(s) which is typically concentrated to about 90 weight percent organic acid(s) before being recycled back to the reactor as an organic acid diluent.

Table 1 below shows the azeotropic compositions of various alkyl acetates used as entrainers. The entrainer to feed ratio is inversely proportional to the mass percent water in the azeotropic composition. Thus, amongst alkyl acetates, the amount of entrainer required decreases with increasing carbon chain length.

TABLE 1

Entrainers for water-acetic acid separation

| Entrainer | Azeotropic Data | | Boiling Point, degrees Celsius |
|---|---|---|---|
| | Weight percent water | Temperature, degrees Celsius | |
| Ethyl acetate | 8 | 70.5 | 77.0 |
| n-propyl acetate | 14 | 82.8 | 101.5 |
| isopropyl acetate | 10 | 76.6 | 88.9 |
| isobutyl acetate | 16 | 87.7 | 116.4 |
| n-butyl acetate | 27 | 90.6 | 126.0 |

Example 1

Heterogeneous Azeotropic Distillation Scheme for Concentrating Acetic Acid Using Isopropyl Acetate This example demonstrates the use of isopropyl acetate as an entrainer. The heterogeneous azeotropic distillation column (HAD) is designed to obtain the desired purity acetic acid product at the column bottom, while obtaining isopropyl acetate/water azeotrope as overheads. The overhead stream when condensed and decanted forms two liquid phases—organic and aqueous. The organic phase comprises mostly isopropyl acetate and the aqueous phase comprises mostly water (an acid free aqueous stream (AFAS)). The entire organic phase is refluxed back to the HAD column to provide enough isopropyl acetate to act as an entrainer. It is then mixed with the feed stream and co-fed to the HAD column. The aqueous phase is drawn out from the system for further treatment or discharge. A portion of the aqueous phase may be refluxed back to the column if the organic reflux falls short of fulfilling the column specifications.

The design basis for the HAD column is shown in Table 2 below.

TABLE 2

Design basis for HAD column - aqueous acetic acid feed

| | |
|---|---|
| Operating Pressure | 101,325 Pascal (1 atm) |
| Flows kg/h (lb/h) | Feed |
| Acetic acid | 19907 (43849) |
| Nitromethane | 29 (63) |
| Nitroethane | 8 (17) |
| 2-nitropropane | 36 (80) |
| 1-nitropropane | 12 (26) |
| 2,2-dinitropropane | 44 (97) |
| Water | 13191 (29056) |
| Percent acid recovery | >99% |

The HAD column consists of 40 equilibrium stages, wherein the 60 weight percent aqueous acetic acid stream (from bottoms of second stripper) is fed to stage 7 from the top. The overheads from HAD column are condensed and then phase separated to yield an organic and an aqueous phase. The entire organic phase and 10 percent of the aqueous phase—is refluxed back to the top of HAD. The column is operated at a design specification of 98 percent recovery of acetic acid in the bottoms. Table 3 below shows input/output stream details of HAD column for the case of isopropyl acetate as an entrainer.

TABLE 3

HAD column stream details with isopropyl acetate as an entrainer

| | Overhead | Bottoms | Organic Phase | Aqueous Phase | AFAS |
|---|---|---|---|---|---|
| Temperature, deg. C. (deg. F.) | 82.6 (180.7) | 108 (226.4) | 42.4 (108.4) | 42.4 (108.4) | 42.4 (108.4) |
| Pressure, Pa (psia) | $10.0 \times 10^4$ (14.5) | $10.0 \times 10^4$ (14.5) | $10.0 \times 10^4$ (14.5) | $10.0 \times 10^4$ (14.5) | $10.0 \times 10^4$ (14.5) |
| Mole Flow, kgmol/h (lbmol/h) | 1507.4 (3323.3) | 448.1 (987.9) | 822.7 (1813.8) | 685.2 (1510.7) | 616.7 (1359.6) |
| Mass Flow, kg/h (lb/h) | 84720.8 (186777.5) | 22021.1 (48548.3) | 72294.0 (159380.9) | 12484.9 (27524.6) | 11236.5 (24772.2) |
| Mass Flow, kg/h (lb/h) | | | | | |
| Water | 14092.9 (31069.5) | 2105.7 (4642.2) | 1788.5 (3942.9) | 12304.4 (27126.6) | 11074.0 (24413.9) |
| Nitromethane | 1235.2 (2723.1) | 0.0 (0.0) | 1203.5 (2653.3) | 31.7 (69.8) | 24.5 (62.8) |
| Nitroethane | 782.5 (1725.1) | 0.0 (0.0) | 773.9 (1706.2) | 8.6 (18.9) | 7.7 (17.0) |
| Acetic Acid | 405.6 (894.1) | 19871.6 (43809.4) | 385.1 (849.1) | 20.4 (45.0) | 18.4 (40.5) |
| 2-nitropropane | 10193.3 (22472.3) | 0.0 (0.0) | 10152.7 (22382.8) | 40.6 (89.4) | 36.5 (80.5) |
| 1-nitropropane | 3622.8 (7986.9) | 0.0 (0.0) | 3609.7 (7958.0) | 13.2 (29.0) | 11.8 (26.1) |
| 2,2-dinitropropane | 0.0 (0.0) | 43.9 (96.7) | 0.0 (0.0) | 0.0 (0.0) | 0.0 (0.0) |
| Isopropyl acetate | 54373.0 (119871.9) | 0.0 | 54366.5 (119857.7) | 64.5 (142.3) | 58.1 (128.1) |
| Mass Fraction | | | | | |
| Water | 0.166 | 0.096 | 0.025 | 0.986 | 0.986 |
| Nitromethane | 0.015 | 0 | 0.017 | 0.003 | 0.003 |
| Nitroethane | 0.009 | 0 | 0.011 | 0.001 | 0.001 |
| Acetic Acid | 0.005 | 0.902 | 0.005 | 0.002 | 0.002 |
| 2-nitropropane | 0.12 | 0 | 0.14 | 0.003 | 0.003 |
| 1-nitropropane | 0.043 | 0 | 0.05 | 0.001 | 0.001 |
| 2,2-dinitropropane | 0 | 0.002 | 0 | 0 | 0 |
| Isopropyl acetate | 0.642 | 0 | 0.752 | 0.005 | 0.005 |

Example 2

Heterogeneous Azeotropic Distillation Scheme for Concentrating Acetic Acid Using n-Butyl Acetate This example demonstrates the use of n-butyl acetate as an entrainer. The HAD column is designed to obtain the desired purity acetic acid product at the column bottom, while obtaining n-butyl acetate/water azeotrope as overheads. The overhead stream when condensed and decanted forms two liquid phases—organic and aqueous. The organic phase comprises mostly n-butyl acetate and the aqueous phase comprises mostly water (an acid free aqueous stream (AFAS)). The entire organic phase is refluxed back to the HAD column to provide enough n-butyl acetate to act as an entrainer. It is then mixed with the feed stream and co-fed to the HAD column.

The aqueous phase is drawn out from the system for further treatment or discharge. A portion of the aqueous phase may be refluxed back to the column if the organic reflux falls short of fulfilling the column specifications.

The HAD column consists of 40 equilibrium stages, wherein the 60 weight percent aqueous acetic acid stream (from bottoms of second stripper) is fed to stage 4 from the top. The overheads from HAD column are condensed and then phase separated to yield an organic and an aqueous phase. The entire organic phase and 20 percent of the aqueous phase—is refluxed back to the top of HAD column. Table 4 below shows input/output stream details of the HAD column for the case of n-butyl acetate as an entrainer.

ing isobutyl acetate/water azeotrope as overheads. The overhead stream when condensed and decanted forms two liquid phases—organic and aqueous. The organic phase comprises mostly isobutyl acetate and the aqueous phase comprises mostly water (an acid free aqueous stream (AFAS)). The entire organic phase is refluxed back to the drying column to provide enough isobutyl acetate to act as an entrainer. It is then mixed with the feed stream and co-fed to the HAD column. The aqueous phase is drawn out from the system for further treatment or discharge. A portion of the aqueous phase may be refluxed back to the column if the organic reflux falls short of fulfilling the column specifications.

TABLE 4

HAD column stream details with n-butyl acetate as an entrainer

|  | Overhead | Bottoms | Organic Phase | Aqueous Phase | AFAS |
|---|---|---|---|---|---|
| Temperature, deg. C. (deg. F.) | 90.4 (194.8) | 108.0 (226.3) | 42.8 (109.1) | 42.8 (109.1) | 42.8 (109.1) |
| Pressure, Pa (psia) | $10.0 \times 10^4$ (14.5) | $10.0 \times 10^4$ (14.5) | $10.0 \times 10^4$ (14.5) | $10.0 \times 10^4$ (14.5) | $10.0 \times 10^4$ (14.5) |
| Mole Flow, kgmol/h (lbmol/h) | 1143.4 (2520.7) | 463.7 (1022.2) | 392.6 (865.5) | 750.8 (1655.3) | 600.7 (1324.3) |
| Mass Flow, kg/h (lb/h) | 51124.9 (112711.1) | 22259.1 (49073.0) | 37447.7 (82558.0) | 13684.1 (30168.3) | 10947.3 (24134.6) |
| Mass Flow, kg/h (lb/h) | | | | | |
| Water | 14278.5 (31478.8) | 2403.3 (5298.3) | 808.0 (1781.4) | 13470.5 (29697.3) | 10776.4 (23757.9) |
| Nitromethane | 599.6 (1321.8) | 0.0 (0.0) | 564.0 (1243.3) | 35.6 (78.5) | 28.5 (62.8) |
| Nitroethane | 369.5 (814.6) | 0.0 (0.0) | 359.9 (793.5) | 9.6 (21.1) | 7.7 (16.9) |
| Acetic Acid | 933.5 (2058.1) | 19812.0 (43678.0) | 836.2 (1843.4) | 97.4 (214.7) | 77.9 (171.8) |
| 2-nitropropane | 4981.9 (10983.2) | 0.0 (0.0) | 4936.0 (10882.0) | 45.9 (101.2) | 36.7 (81.0) |
| 1-nitropropane | 2518.9 (5553.2) | 0.0 (0.0) | 2504.2 (5520.8) | 14.7 (32.4) | 11.7 (25.9) |
| 2,2-dinitropropane | 0.0 (0.0) | 43.9 (96.7) | 0.0 (0.0) | 0.0 (0.0) | 0.0 (0.0) |
| n-butyl acetate | 27435.5 (60484.9) | 0.0 (0.0) | 27433.7 (60481.1) | 8.6 (18.9) | 6.8 (15.1) |
| Mass Fraction | | | | | |
| Water | 0.279 | 0.108 | 0.022 | 0.984 | 0.984 |
| Nitromethane | 0.012 | 0 | 0.015 | 0.003 | 0.003 |
| Nitroethane | 0.007 | 0 | 0.01 | 0.001 | 0.001 |
| Acetic Acid | 0.018 | 0.89 | 0.022 | 0.007 | 0.007 |
| 2-nitropropane | 0.097 | 0 | 0.132 | 0.003 | 0.003 |
| 1-nitropropane | 0.049 | 0 | 0.067 | 0.001 | 0.001 |
| 2,2-dinitropropane | 0 | 0.002 | 0 | 0 | 0 |
| n-butyl acetate | 0.537 | 0 | 0.733 | 0.001 | 0.001 |

Example 3

Heterogeneous Azeotropic Distillation Scheme for Concentrating Acetic Acid Using Isobutyl Acetate This example demonstrates the use of isobutyl acetate as an entrainer. The HAD column is designed to obtain the desired purity acetic acid product at the column bottom, while obtain- The HAD column consists of 40 equilibrium stages, wherein the 60 weight percent aqueous acetic acid stream (from bottoms of second stripper) is fed to stage 16 from the top. The overheads from HAD column are condensed and then phase separated to yield an organic and an aqueous phase. The entire organic phase and 4 percent of the aqueous phase—is refluxed back to the top of HAD column. Table 5 below shows input/output stream details of HAD column for the case of isobutyl acetate as an entrainer.

TABLE 5

HAD column stream details with isobutyl acetate as an entrainer

|  | Overhead | Bottoms | Organic Phase | Aqueous Phase | AFAS |
|---|---|---|---|---|---|
| Temperature, deg. C. (deg. F.) | 90.6 (195) | 110.4 (230.8) | 33.6 (92.4) | 33.6 (92.4) | 33.6 (92.4) |
| Pressure, Pa (psia) | $10.0 \times 10^4$ (14.5) | $10.0 \times 10^4$ (14.5) | $10.0 \times 10^4$ (14.5) | $10.0 \times 10^4$ (14.5) | $10.0 \times 10^4$ (14.5) |
| Mole Flow, kgmol/h (lbmol/h) | 1173.9 (2587.9) | 410.8 (905.7) | 493.1 (1087.2) | 681.2 (1501.8) | 653.9 (1441.7) |

TABLE 5-continued

HAD column stream details with isobutyl acetate as an entrainer

|  | Overhead | Bottoms | Organic Phase | Aqueous Phase | AFAS |
|---|---|---|---|---|---|
| Mass Flow, kg/h (lb/h) | 61231.3 (134991.9) | 21337.8 (47041.9) | 48873.3 (107747.1) | 12413.2 (27366.4) | 11916.6 (26271.7) |
| Mass Flow, kg/h (lb/h) | | | | | |
| Water | 12912.5 (28467.2) | 1438.2 (3170.6) | 681.5 (1502.4) | 12231.0 (26964.7) | 11741.7 (25886.1) |
| Nitromethane | 760.4 (1676.4) | 0.0 (0.0) | 730.7 (1611.0) | 29.7 (65.4) | 28.5 (62.8) |
| Nitroethane | 479.9 (1057.9) | 0.0 (0.0) | 471.9 (1040.3) | 8.0 (17.6) | 7.7 (16.9) |
| Acetic Acid | 827.4 (1824.0) | 19855.9 (43774.7) | 791.8 (1745.6) | 35.6 (78.4) | 34.1 (75.2) |
| 2-nitropropane | 6775.2 (14936.8) | 0.0 (0.0) | 6737.3 (14853.3) | 37.9 (83.5) | 36.4 (80.2) |
| 1-nitropropane | 3227.6 (7115.7) | 0.0 (0.0) | 3215.4 (7088.8) | 12.2 (26.9) | 11.7 (25.8) |
| 2,2-dinitropropane | 0.0 (0.0) | 43.9 (96.7) | 0.0 (0.0) | 0.0 (0.0) | 0.0 (0.0) |
| Isobutyl acetate | 36242.3 (79878.5) | 0.0 (0.0) | 36230.0 (79873.4) | 57.4 (126.6) | 55.1 (121.5) |
| Mass Fraction | | | | | |
| Water | 0.211 | 0.067 | 0.014 | 0.985 | 0.985 |
| Nitromethane | 0.012 | 0 | 0.015 | 0.002 | 0.002 |
| Nitroethane | 0.008 | 0 | 0.01 | 0.001 | 0.001 |
| Acetic Acid | 0.014 | 0.931 | 0.016 | 0.003 | 0.003 |
| 2-nitropropane | 0.111 | 0 | 0.138 | 0.003 | 0.003 |
| 1-nitropropane | 0.053 | 0 | 0.066 | 0.001 | 0.001 |
| 2,2-dinitropropane | 0 | 0.002 | 0 | 0 | 0 |
| Isobutyl acetate | 0.592 | 0 | 0.741 | 0.005 | 0.005 |

Table 6 below compares the design parameters of the HAD column using isopropyl acetate, n-butyl acetate, and isobutyl acetate. The entrainer-to-feed ratio is maximum in the case of isopropyl acetate on account of its low water content (10 weight percent) at the azeotropic composition—as compared to iso and n-butyl acetate (16 and 27 weight percent respectively). The reboiler duty required in case of n-butyl acetate is the lowest; however the acetic acid slip in AFAS stream is the highest amongst the three candidate entrainers. Also, any slip of n-butyl actetate back to the reactor can result in generation of unwanted byproducts which may contaminate the final product—which would not be the case with isobutyl acetate.

TABLE 6

Comparison of HAD column design parameters for iso-propyl acetate, n-butyl acetate, and isobutyl acetate

|  |  | Feed Streams |  | Energy Duty |  |  |  |  | Acid slip in AFAS, kg/h (lb/h) | Fraction of aqu. stream as reflux | % acid recovery |
|---|---|---|---|---|---|---|---|---|---|---|---|
|  | No. of equilibrium stages | Aqu. Feed stream | Organic reflux | J/s (MMBTU/h) | J/kg feed (BTU/lb feed) | Entrainer feed, kg (lb) | Entrainer: feed ratio (mass) | Wt % acid in bottoms |  |  |  |
| Isopropyl acetate | 40 | 7 | 1 | $1.7 \times 10^7$ (59.7) | $1.9 \times 10^6$ (815.2) | 54431.1 (120000.0) | 1.64 | 90.2 | 18.4 (40.5) | 0.1 | 99.9 |
| n-butyl acetate | 40 | 4 | 1 | $1.5 \times 10^7$ (47.7) | $1.5 \times 10^6$ (651.7) | 27442.3 (60500) | 0.83 | 89 | 77.9 (171.8) | 0.2 | 99.6 |
| Isobutyl acetate | 40 | 16 | 1 | $1.5 \times 10^7$ (50.1) | $1.6 \times 10^6$ (684.5) | 36287.4 (80000) | 1.09 | 93.1 | 34.1 (75.2) | 0.04 | 99.8 |

Example 4

Heterogeneous Azeotropic Distillation Scheme for Concentrating an Aqueous Mixed Acid Stream Comprising Acetic Acid, Propionic Acid, and Butyric Acid Using Isobutyl Acetate This example illustrates the use of isobutyl acetate as an entrainer for concentrating an aqueous mixed acid feed stream comprising of acetic acid, propionic acid and butyric acid. The design basis for HAD column is shown in Table 7 below.

TABLE 7

Design basis for HAD column - aqueous mixed acid feed

| Operating Pressure | 101,325 Pascal (1 atm) |
|---|---|
| Flows kg/h (lb/h) | Feed |
| Acetic acid | 13338 (29380) |
| Propionic acid | 3284 (7233) |
| Butyric acid | 3284 (7233) |
| Nitromethane | 29 (63) |
| Nitroethane | 8 (17) |
| 2-nitropropane | 36 (80) |

TABLE 7-continued

Design basis for HAD column - aqueous mixed acid feed

| 1-nitropropane | 12 (26) |
|---|---|
| 2,2-dinitropropane | 44 (97) |
| Water | 13191 (29056) |
| Percent total acid recovery | >99% |

Table 8 below shows input/output stream details of the HAD column for the case of isobutyl acetate as an entrainer for mixed acid feed.

TABLE 8

HAD column stream details with isobutyl acetate as an entrainer - mixed acid (acetic:propionic:butyric) feed

|  | Overhead | Bottoms | Organic Phase | Aqueous Phase | AFAS |
|---|---|---|---|---|---|
| Temperature, deg. C. (deg. F.) | 89.4 (192.9) | 107.6 (225.7) | 32.4 (90.4) | 32.4 (90.4) | 32.4 (90.4) |
| Pressure, Pa (psia) | $10.0 \times 10^4$ (14.5) | $10.0 \times 10^4$ (14.5) | $10.0 \times 10^4$ (14.5) | $10.0 \times 10^4$ (14.5) | $10.0 \times 10^4$ (14.5) |
| Mole Flow, kgmol/h (lbmol/h) | 1085.2 (2392.5) | 437.8 (965.1) | 461.5 (1017.4) | 624.2 (1376.1) | 599.2 (1321.1) |
| Mass Flow, kg/h (lb/h) | 58629.4 (129255.7) | 22295.6 (49153.3) | 47270.7 (104214.1) | 11413.3 (25162.1) | 10956.8 (24155.6) |
| Mass Flow, kg/h (lb/h) |  |  |  |  |  |
| Water | 11788.6 (25989.5) | 2437.3 (5373.3) | 598.4 (1319.2) | 11190.2 (24670.2) | 10742.6 (23683.4) |
| Nitromethane | 754.6 (1663.5) | 2.3 (5.1) | 727.3 (1603.4) | 27.3 (60.1) | 26.2 (57.7) |
| Nitroethane | 226.0 (498.2) | 4.4 (9.6) | 222.6 (490.7) | 3.4 (7.5) | 3.3 (7.2) |
| Acetic acid | 242.6 (534.8) | 13234.0 (29176.0) | 146.4 (322.8) | 96.2 (212.0) | 92.3 (203.5) |
| 2-nitropropane | 7100.1 (15653.0) | 0.0 (0.0) | 7062.3 (15569.6) | 37.8 (83.4) | 36.3 (80.0) |
| 1-nitropropane | (0.6) 1.4 | 12.0 (26.4) | (0.6) 1.4 | 0.0 (0.0) | 0.0 (0.0) |
| Isobutyl acetate | 38500.7 (84879.5) | 0.0 (0.0) | 38498.4 (84874.5) | 56.9 (125.4) | 54.6 (120.4) |
| Propionic acid | 0.0 (0.0) | 3280.9 (7233.2) | 0.0 (0.0) | 0.0 (0.0) | 0.0 (0.0) |
| Butyric acid | 0.0 (0.0) | 3280.9 (7233.2) | 0.0 (0.0) | 0.0 (0.0) | 0.0 (0.0) |
| 2,2-dinitropropane | 0.0 (0.0) | 43.9 (96.7) | 0.0 (0.0) | 0.0 (0.0) | 0.0 (0.0) |
| Mass Fraction |  |  |  |  |  |
| Water | 0.201 | 0.109 | 0.013 | 0.980 | 0.980 |
| Nitromethane | 0.013 | 0.000 | 0.015 | 0.002 | 0.002 |
| Nitroethane | 0.004 | 0.000 | 0.005 | 0.000 | 0.000 |
| Acetic acid | 0.004 | 0.594 | 0.003 | 0.008 | 0.008 |
| 2-nitropropane | 0.121 | 0.000 | 0.149 | 0.003 | 0.003 |
| 1-nitropropane | 0.000 | 0.001 | 0.000 | 0.000 | 0.000 |
| Isobutyl acetate | 0.657 | 0.000 | 0.814 | 0.005 | 0.005 |
| Propionic acid | 0.000 | 0.147 | 0.000 | 0.000 | 0.000 |
| Butyric acid | 0.000 | 0.147 | 0.000 | 0.000 | 0.000 |
| 2,2-dinitropropane | 0.000 | 0.002 | 0.000 | 0.000 | 0.000 |

Table 9 below shows the design parameters of the HAD column for concentrating a mixed acid feed using isobutyl acetate. An overall acid recovery of about 99.5 percent is achieved using isobutyl acetate as an entrainer in the HAD column.

TABLE 9

Design parameters for mixed acid feed to HAD column using isobutyl acetate as an entrainer

|  | Feed Streams | | Energy Duty | | Entrainer feed, kg (lb) | Entrainer: feed ratio (mass) | Wt % acid in bottoms | AFAS, kg/h (lb/h) | Acid slip in stream as reflux | Fraction of aqu. % acid recovery |
|---|---|---|---|---|---|---|---|---|---|---|
|  | No. of equilibrium stages | Aqu. Feed stream | Organic reflux | J/s (MMBTU/h) | J/kg feed (BTU/lb feed) | | | | | | |
| Isobutyl acetate mixed acid feed | 40 | 16 | 1 | $6.3 \times 10^6$ (21.6) | $6.9 \times 10^5$ (295.1) | 38555 (85000) | 1.16 | 89.1 | 92.1 (203) | 0.04 | 99.5 |

Example 5

Heterogeneous Azeotropic Distillation Scheme for Concentrating an Aqueous Mixed Acid Stream Comprising 50 Weight Percent Acetic Acid and 50 Weight Percent Propionic Acid Using Isobutyl Acetate This example illustrates the use of isobutyl acetate as an entrainer for concentrating an aqueous mixed acid feed stream comprising of 50:50 (weight percent) ratio acetic acid and propionic acid. The design basis for HAD column is shown in Table 10 below.

TABLE 10

| Design basis for HAD column - mixed acid feed (acetic:propionic) | |
|---|---|
| Operating Pressure | 101,325 Pascal (1 atm) |
| Flows kg/h (lb/h) | Feed |
| Acetic acid | 9954 (21925) |
| Propionic acid | 9964 (21925) |
| Nitromethane | 29 (63) |
| Nitroethane | 8 (17) |
| 2-nitropropane | 36 (80) |
| 1-nitropropane | 12 (26) |
| 2,2-dinitropropane | 44 (97) |
| Water | 13191 (29056) |
| Percent total acid recovery | >99% |

Table 11 below shows input/output stream details of HAD column for the case of isobutyl acetate as an entrainer for a mixed acid feed (acetic:propionic)

TABLE 11

HAD stream details with isobutyl acetate as an entrainer - mixed acid (acetic:propionic) feed

| | Overhead | Bottoms | Organic Phase | Aqueous Phase | AFAS |
|---|---|---|---|---|---|
| Temperature, deg. C. (deg. F.) | 88.3 (191.0) | 109.7 (229.5) | 32.6 (90.7) | 32.5 (90.7) | 32.6 (90.7) |
| Pressure, Pa (psia) | $10.0 \times 10^4$ (14.5) | $10.0 \times 10^4$ (14.5) | $10.0 \times 10^4$ (14.5) | $10.0 \times 10^4$ (14.5) | $10.0 \times 10^4$ (14.5) |
| Mole Flow, kgmol/h (lbmol/h) | 1110.0 (2447.2) | 403.7 (890.0) | 454.6 (1002.2) | 655.9 (1446.1) | 629.7 (1388.3) |
| Mass Flow, kg/h (lb/h) | 58648.2 (129297.2) | 21772.4 (47999.9) | 46742.5 (103049.6) | 11964.0 (26376.2) | 11485.5 (25321.1) |
| Mass Flow, kg/h (lb/h) | | | | | |
| Water | 12358.6 (27246.0) | 1878.7 (4141.9) | 586.5 (1293.1) | 11772.0 (25952.9) | 11301.2 (24914.8) |
| Nitromethane | 727.1 (1603.0) | 1.8 (4.0) | 699.3 (1541.8) | 27.8 (61.2) | 26.7 (58.8) |
| Nitroethane | 235.5 (519.1) | 4.0 (8.9) | 231.7 (510.8) | 3.8 (8.3) | 3.6 (8.0) |
| Acetic Acid | 150.5 (331.9) | 9885.5 (21793.7) | 88.5 (195.1) | 62.0 (136.7) | 59.6 (131.3) |
| 2-nitropropane | 6664.5 (14692.6) | 0.0 (0.0) | 6626.8 (14609.5) | 37.7 (83.2) | 36.2 (79.8) |
| 1-nitropropane | 1.1 (2.4) | 12.0 (26.4) | 1.0 (2.3) | 0.0 (0.0) | 0.0 (0.0) |
| Isobutyl acetate | 38495.5 (84868.1) | 1.5 (3.3) | 38494.7 (84866.2) | 59.2 (130.5) | 56.8 (125.3) |
| Propionic acid | 0.0 (0.0) | 9945.0 (21925.0) | 0.0 (0.0) | 0.0 (0.0) | 0.0 (0.0) |
| 2,2-dinitropropane | 0.0 (0.0) | 43.9 (96.7) | 0.0 (0.0) | 0.0 (0.0) | 0.0 (0.0) |
| Mass Fraction | | | | | |
| Water | 0.211 | 0.086 | 0.013 | 0.984 | 0.984 |
| Nitromethane | 0.012 | 0.000 | 0.015 | 0.002 | 0.002 |
| Nitroethane | 0.004 | 0.000 | 0.005 | 0.000 | 0.000 |
| Acetic Acid | 0.003 | 0.454 | 0.002 | 0.005 | 0.005 |
| 2-nitropropane | 0.114 | 0.000 | 0.142 | 0.003 | 0.003 |
| 1-nitropropane | 0.000 | 0.001 | 0.000 | 0.000 | 0.000 |
| Isobutyl acetate | 0.656 | 0.000 | 0.824 | 0.005 | 0.005 |
| Propionic acid | 0.000 | 0.457 | 0.000 | 0.000 | 0.000 |
| 2,2-dinitropropane | 0.000 | 0.002 | 0.000 | 0.000 | 0.000 |

Table 12 below shows the design parameters of HAD column for concentrating a mixed acid feed (acetic:propionic acid) stream using isobutyl acetate. An overall acid recovery of about 99.6 percent is achieved using isobutyl acetate as an entrainer in the HAD column.

TABLE 12

Design parameters for HAD column using isobutyl acetate as an entrainer

| | No. of equilibrium stages | Feed Streams | | Energy Duty | | Entrainer feed, kg (lb) | Entrainer: feed ratio (mass) | Wt % acid in bottoms | Acid slip in AFAS, kg/h (lb/h) | Fraction of aqu. stream as reflux | % acid recovery |
|---|---|---|---|---|---|---|---|---|---|---|---|
| | | Aqu. Feed stream | Organic reflux | J/s (MMBTU/h) | J/kg feed (BTU/lb feed) | | | | | | |
| Isobutyl acetate mixed acid feed | 40 | 16 | 1 | $4.1 \times 10^6$ (14.1) | $4.5 \times 10^5$ (192.65) | 38555.4 (85000) | 1.16 | 91 | 57.2 (126) | 0.04 | 99.7 |

Example 6

Heterogeneous Azeotropic Distillation Scheme for Concentrating an Aqueous Mixed Acid Stream Comprising 50 Weight Percent Propionic Acid and 50 Weight Percent n-Butyric Acid Using Isobutyl Acetate This example illustrates the use of isobutyl acetate as an entrainer for concentrating an aqueous mixed acid feed stream comprising of 50:50 (weight percent) ratio propionic acid and n-butyric acid. The design basis for HAD column is shown in Table 13 below.

TABLE 13

Design basis for HAD column - mixed acid feed (propionic:n-butyric)

| | |
|---|---|
| Operating Pressure | 101,325 Pascal (1 atm) |
| Flows kg/h (lb/h) | Feed |

TABLE 13-continued

Design basis for HAD column - mixed acid feed (propionic:n-butyric)

| | |
|---|---|
| Propionic acid | 9954 (21925) |
| n-butyric acid | 9964 (21925) |
| Nitromethane | 29 (63) |
| Nitroethane | 8 (17) |
| 2-nitropropane | 36 (80) |
| 1-nitropropane | 12 (26) |
| 2,2-dinitropropane | 44 (97) |
| Water | 13191 (29056) |
| Percent total acid recovery | >99% |

Table 14 below shows input/output stream details of HAD column for the case of isobutyl acetate as an entrainer for a mixed acid feed (propionic:n-butyric).

TABLE 14

HAD column stream details with isobutyl acetate as an entrainer - mixed acid (propionic:n-butyric) feed

| | Overhead | Bottoms | Organic Phase | Aqueous Phase | AFAS |
|---|---|---|---|---|---|
| Temperature, deg. C. (deg. F.) | 83.2 (181.7) | 109.8 (229.7) | 33.8 (92.9) | 33.8 (92.9) | 33.8 (92.9) |
| Pressure, Pa (psia) | $10.0 \times 10^4$ (14.5) | $10.0 \times 10^4$ (14.5) | $10.0 \times 10^4$ (14.5) | $10.0 \times 10^4$ (14.5) | $10.0 \times 10^4$ (14.5) |
| Mole Flow, kgmol/h - (lbmol/h) | 923.3 (2035.6) | 340.1 (749.7) | 283.2 (624.3) | 640.7 (1412.4) | 640.7 (1412.4) |
| Mass Flow, kg/h (lb/h) | 40707.0 (89743.6) | 21590.0 (47597.7) | 29096.8 (64147.4) | 11668.9 (25725.6) | 11668.9 (25725.6) |
| Mass Flow, kg/h (lb/h) | | | | | |
| Water | 11877.7 (26185.9) | 1672.7 (3687.6) | 370.4 (816.7) | 11507.3 (25369.2) | 11507.3 (25369.2) |
| Nitromethane | 432.7 (954.0) | 2.9 (6.5) | 407.2 (897.7) | 25.5 (56.3) | 25.5 (56.3) |
| Nitroethane | 242.2 (533.9) | 1.6 (3.5) | 236.1 (520.6) | 6.1 (13.4) | 6.1 (13.4) |
| 2-nitropropane | 3244.0 (7151.8) | 7.3 (16.1) | 3214.6 (7086.9) | 29.4 (64.9) | 29.4 (64.9) |
| 1-nitropropane | 765.4 (1687.5) | 4.3 (9.5) | 757.8 (1670.6) | 7.7 (16.9) | 7.7 (16.9) |
| Isobutyl acetate | 23981.7 (52870.6) | 0.0 (0.0) | 23981.7 (52870.5) | 58.7 (129.5) | 58.7 (129.5) |
| Propionic acid | 151.0 (332.8) | 9912.4 (21853.0) | 118.3 (260.7) | 32.7 (72.1) | 32.7 (72.1) |
| n-butyric acid | 2.2 (4.9) | 9945.0 (21924.9) | 2.1 (4.7) | 0.05 (0.1) | 0.05 (0.1) |
| 2,2-dinitropropane | 0.0 (0.0) | 43.9 (96.7) | 0.0 (0.0) | 0.0 (0.0) | 0.0 (0.0) |

TABLE 14-continued

HAD column stream details with isobutyl acetate as an entrainer - mixed acid (propionic:n-butyric) feed

| | Overhead | Bottoms | Organic Phase | Aqueous Phase | AFAS |
|---|---|---|---|---|---|
| Mass Fraction | | | | | |
| Water | 0.292 | 0.077 | 0.013 | 0.986 | 0.986 |
| Nitromethane | 0.011 | 0 | 0.014 | 0.002 | 0.002 |
| Nitroethane | 0.006 | 0 | 0.008 | 0.001 | 0.001 |
| 2-nitropropane | 0.08 | 0 | 0.11 | 0.003 | 0.003 |
| 1-nitropropane | 0.019 | 0 | 0.026 | 0.001 | 0.001 |
| Isobutyl acetate | 0.589 | 0 | 0.824 | 0.005 | 0.005 |
| Propionic acid | 0.004 | 0.459 | 0.004 | 0.003 | 0.003 |
| n-butyric acid | 0 | 0.461 | 0 | 0 | 0 |
| 2,2-dinitropropane | 0 | 0.002 | 0 | 0 | 0 |

Table 15 below shows the design parameters of HAD column for concentrating a mixed acid feed (propionic acid:n-butyric acid) stream using isobutyl acetate. An overall acid recovery of about 99.7 percent is achieved using isobutyl acetate as an entrainer in the HAD column.

TABLE 15

Design parameters for HAD column using isobutyl acetate as an entrainer (propionic:n-butyric) feed

| | | Feed Streams | | Energy Duty | | | | | Acid slip in stream as reflux | Fraction of aqu. |
|---|---|---|---|---|---|---|---|---|---|---|
| | No. of equilibrium stages | Aqu. Feed stream | Organic reflux | J/s (MMBTU/h) | J/kg feed (BTU/lb feed) | Entrainer feed, kg (lb) | Entrainer: feed ratio (mass) | Wt % acid in bottoms | AFAS, kg/h (lb/h) | | % acid recovery |
| Isobutyl acetate mixed acid feed | 40 | 16 | 1 | 2.8 × 10⁶ (9.5) | 3.0 × 10⁵ 129.8 | 24040.4 (53000) | 0.72 | 92.3 | 57.2 (126) | 0 | 99.85 |

Experimental Example

The use of isobutyl acetate as an entrainer is also demonstrated experimentally. Example 7 is completed on a continuous distillation column as shown in FIG. 3. This column is constructed of 316L stainless steel. The tower inner diameter is 6.36 inches and is approximately 24 feet tall. The packing consists of four, 5' 3.3" sections of 1T Intalox® structured packing. The temperature profile is measured using temperature probes located at approximately the middle of each packing section, as shown in FIG. 4. Distributor trays are located between each packing section in order to maintain liquid distribution. The distributor trays also permit the feed location to be varied. The column is equipped with a pump around reboiler. Heat is provided using 2.8×10⁶ Pascal (40 psi) steam. The overhead product is condensed using cooling water. A decanter is available to phase separate and reflux a single phase from a heterogeneous azeotrope. The column may be operated at pressures from full vacuum (5 mm Hg) up to 5.2×10⁵ Pascal (75 psi). A feed blend of about 60 weight percent acetic acid and 40 weight percent deionized water is prepared to test the performance of isobutyl acetate as the entrainer.

Example 7

Table 16 below shows a capability to minimize acetic acid losses in the overhead stream if more isobutyl acetate is allowed in the bottom stream.

TABLE 16

| Temperature Point | Temperature; degrees Celcius (degrees Fahrenheit) |
|---|---|
| 1 | 111 (232) |
| 2 | 102 (216) |
| 3 | 92 (198) |
| 4 | 88 (190) |
| 5 | 87 (189) |
| 6 | 88 (190) |
| Feed; kg/h (lb/h) | 13.6 (30) |
| Reflux; kg/h (lb/h) | 18.1 (40) |
| Water Take Off; kg/h (lb/h) | 6.8 (15) |
| Steam; kg/h (lb/h) | 7.7 (17) |
| Acetic acid in overhead water phase (wt %) | 0.38 |
| Acetic acid in bottom phase (wt %) | 89.8 |
| Isobutyl acetate in bottom phase (wt %) | 0.133 |
| Water in bottom phase (wt %) | 8.64 |
| Total bottom phase (wt %) | 98.573 |

Figure 5:
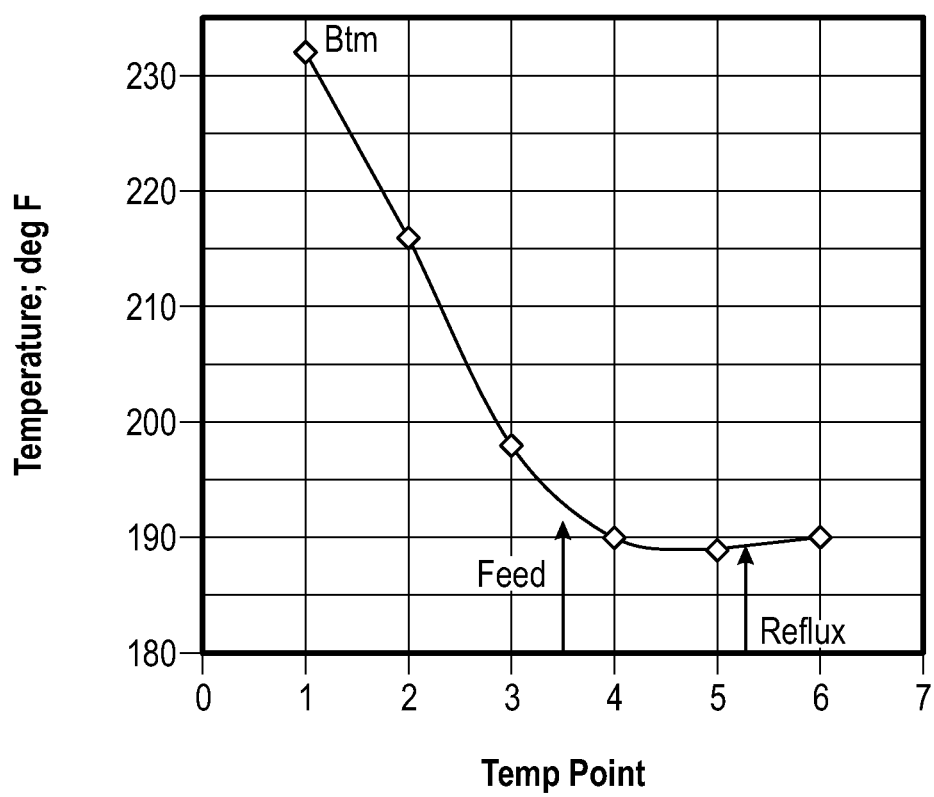
FIG. 5 is a graph of the temperature profile for Example 7.

FIG. 5 shows the temperature profile during the experiments in Table 16.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process comprising:
reacting a gaseous hydrocarbon feedstock with a liquid aqueous feedstock in a reactor at a reaction temperature of at least 140° C. and less than 325° C. and a reaction pressure of at least 6.8×10⁶ Pascal in a high pressure nitration process to produce a product stream comprising a nitroalkane and byproducts, wherein the liquid aqueous feedstock comprises at least about 40 weight percent of a first organic acid;
processing the product stream to produce a first top stream and a first bottom stream, wherein the first top stream comprises the nitroalkane and the first bottom stream comprises the first organic acid and water;
supplying at least a portion of the first bottom stream to an azeotropic distillation column;
using an alkyl acetate as an entrainer in the azeotropic distillation column, such that the first bottom stream is separated into at least a second top stream and a second bottom stream, wherein the second top stream comprises the alkyl acetate and water and wherein the second bottom stream comprises the first organic acid;
separating the second top stream in a phase separator into an organic phase and an aqueous phase, the organic phase comprising the alkyl acetate; and
returning at least a portion of the organic phase to the azeotropic distillation column.

2. A process according to claim 1, wherein the liquid aqueous feedstock further comprises water and between about 10 and 50 weight percent of nitric acid.

3. A process according to claim 1, wherein the first organic acid is selected from the group consisting of acetic acid, propionic acid, butyric acid, and any combination thereof.

4. A process according to claim 1, wherein the first bottom stream further comprises at least a second organic acid.

5. A process according to claim 4, wherein the second organic acid is selected from the group consisting of acetic acid, propionic acid, butyric acid, and any combination thereof, and wherein the second organic acid is different than the first organic acid.

6. A process according to claim 4, wherein the first bottom stream further comprises at least a third organic acid.

7. A process according to claim 6, wherein the third organic acid is selected from the group consisting of acetic acid, propionic acid, butyric acid, and any combination thereof, and wherein the third organic acid is different than the first organic acid and the second organic acid.

8. A process according to claim 1, wherein the first organic acid is present in the second bottom stream in a higher concentration than in the first bottom stream.

9. A process according to claim 1, further comprising returning at least a portion of the second bottom stream to the reactor.

10. A process comprising:
reacting a gaseous hydrocarbon feedstock with a liquid aqueous feedstock in a reactor at a reaction temperature of at least 140° C. and less than 325° C. and a reaction pressure of at least 6.8×10⁶ Pascal in a high pressure nitration process in a high pressure nitration process to produce a product stream comprising a nitroalkane and byproducts, wherein the liquid aqueous feedstock comprises water, nitric acid, a first organic acid, and a second organic acid, and wherein the first organic acid and the second organic acid comprise at least about 40 weight percent of the liquid aqueous feedstock;
processing the product stream to produce a first top stream and a first bottom stream, wherein the first top stream comprises the nitroalkane and the first bottom stream comprises the first organic acid, the second organic acid, and water;
supplying at least a portion of the first bottom stream to an azeotropic distillation column;
using an alkyl acetate as an entrainer in the azeotropic distillation column, such that the first bottom stream is separated into at least a second top stream and a second bottom stream, wherein the second top stream comprises the alkyl acetate and water and wherein the second bottom stream comprises the first organic acid and the second organic acid;
separating the second top stream in a phase separator into an organic phase and an aqueous phase, the organic phase comprising the alkyl acetate; and
returning at least a portion of the organic phase to the azeotropic distillation column.

* * * * *

UNITED STATES PATENT AND TRADEMARK OFFICE
CERTIFICATE OF CORRECTION

PATENT NO.        : 9,133,094 B2  
APPLICATION NO.   : 14/007531  
DATED             : September 15, 2015  
INVENTOR(S)       : Sawant et al.

Page 1 of 1

It is certified that error appears in the above-identified patent and that said Letters Patent is hereby corrected as shown below:

In the claims

Claim 10, Column 24, line 19

Delete the words "in a high pressure nitration process" therefor.

Signed and Sealed this  
Twenty-ninth Day of March, 2016

Michelle K. Lee  
*Director of the United States Patent and Trademark Office*